United States Patent
Pierson, III

(10) Patent No.: US 6,648,903 B1
(45) Date of Patent: *Nov. 18, 2003

(54) MEDICAL TENSIONING SYSTEM

(76) Inventor: Raymond H. Pierson, III, 62 Columbia St. Suite 102, Orlando, FL (US) 32806

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,354

(22) Filed: Sep. 8, 1998

(51) Int. Cl.$^7$ .............................. A61B 17/68
(52) U.S. Cl. ........................... 606/232; 73/74
(58) Field of Search ................. 606/73, 74, 103, 606/232, 72, 75

(56) References Cited

U.S. PATENT DOCUMENTS

| | | | |
|---|---|---|---|
| 2,472,009 A | * | 5/1949 | Gardner |
| 5,127,413 A | | 7/1992 | Ebert |
| 5,372,146 A | | 12/1994 | Branch |
| 5,611,801 A | | 3/1997 | Songer |
| 5,797,915 A | | 8/1998 | Pierson, III et al. |
| 5,957,953 A | * | 9/1999 | DiPoto et al. ............... 606/232 |
| 5,972,022 A | * | 10/1999 | Huxel ......................... 606/215 |
| 5,993,475 A | * | 11/1999 | Lin et al. ..................... 606/213 |

FOREIGN PATENT DOCUMENTS

| GB | 2188237 | 9/1987 |
|---|---|---|
| WO | WO 96/09797 | 4/1996 |

* cited by examiner

*Primary Examiner*—Michael H. Thaler
(74) *Attorney, Agent, or Firm*—Allen, Dyer, Doppelt, Milbrath & Gilchrist, P.A.

(57) ABSTRACT

A medical tensioning cable system provides dynamic tensioning to maintain high tension in a fixation system despite tissue shifting, cable slippage, or other inadvertent loss of tension. An exemplary embodiment of an in-line dynamic tensioning system includes a dynamically tensioning cable retainer, suitably comprising a suture anchor or bone screw, which provides a bias to maintain tension in the cable after installation. The retainer includes a retaining mechanism for retaining the cable or suture and a biasing mechanism connected to the retaining mechanism. In the event of cable slippage or slackening, the biasing mechanism tends to take up the slack and maintain tension. As a result, cable tension is maintained regardless of inadvertent cable slackening after installation.

4 Claims, 14 Drawing Sheets

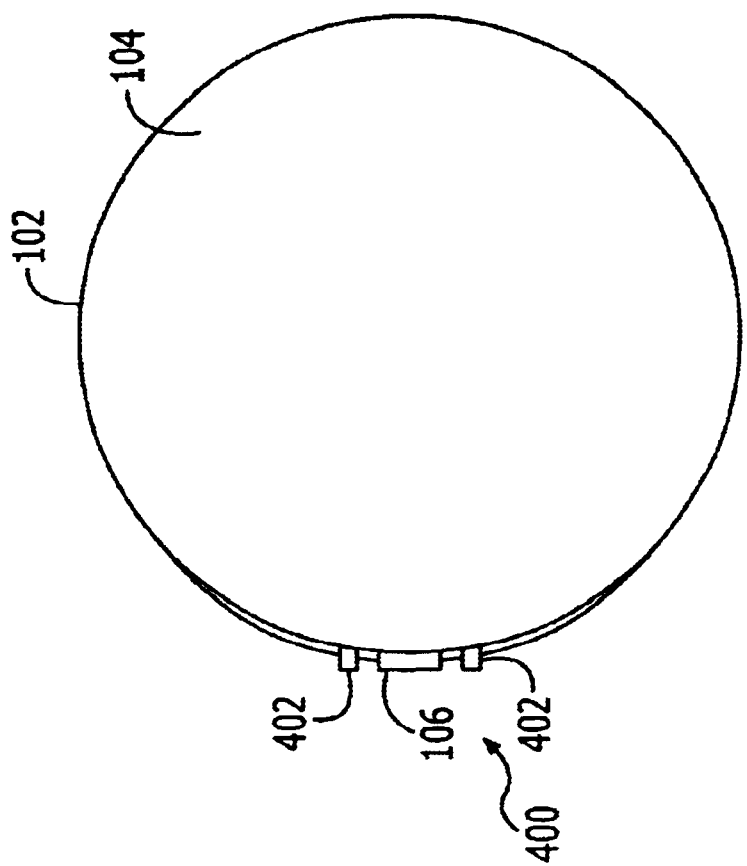

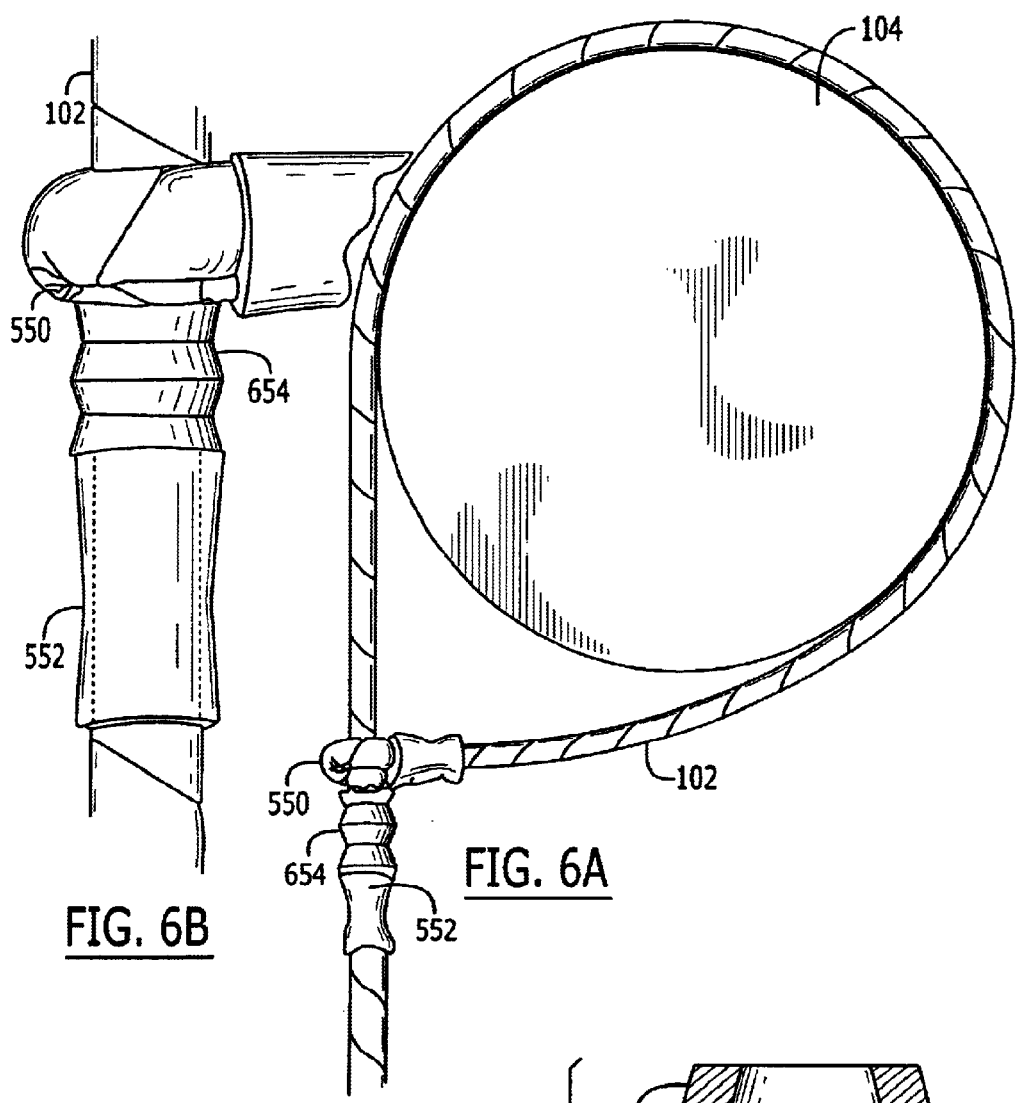

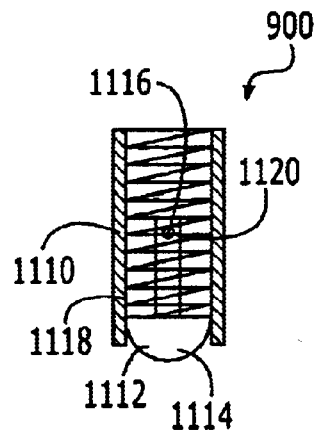
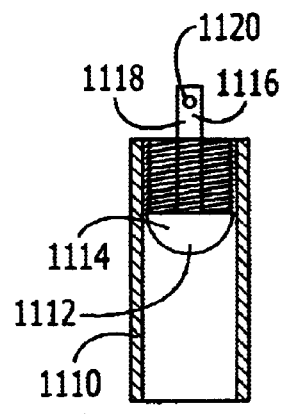
FIG. 11A FIG. 11B
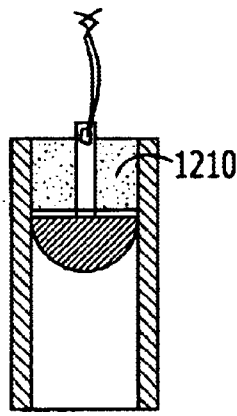
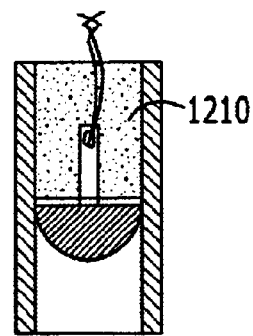
FIG. 12A FIG. 12B
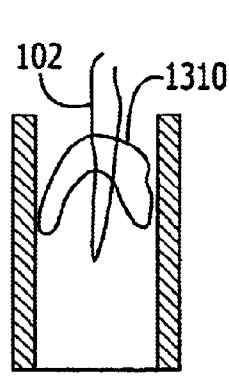
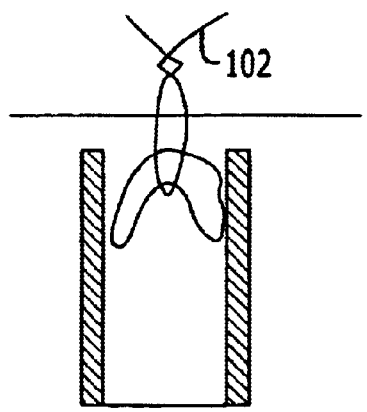
FIG. 13A FIG. 13B

MEDICAL TENSIONING SYSTEM

BACKGROUND OF THE INVENTION

1. Field of the Invention

The invention generally relates to surgical implements, and more particularly, to medical tensioning and retaining systems.

2. Description of the Related Art

Medical fixation of skeletal structures is an important procedure for orthopedic surgeons. Surgeons use fixation systems in a variety of applications, including spine fusions, hip arthroplasty, fracture fixation, sternum closures, and the like. Certain fixation systems, such as cerclage systems, include a wire, cable, or suture wrapped tightly around the relevant bone or other structure and fixed in place. The cable usually comprises a wire or cable of biocompatible material, which is fixed in place by either twisting the free ends together or applying a retainer after an appropriate amount of tension has been placed on the wire or cable. The most common retainer is a sleeve which is crimped onto the wire or cable.

Achieving the appropriate tension is vital to the proper functioning of the fixation system. For example, excessive tension in a cerclage cable can cause cable failure, bone fracture, or avascular necrosis of the bone around which the cable is wound. On the other hand, insufficient tensioning prevents the system from performing properly; sufficient tension must be maintained for proper fixation. Furthermore, the tensioning process is often difficult due to the small components and the high tensions required.

Various systems are available for applying and measuring cable tension. For example, both the Howmedica Dall Miles System and DePuy Control Cable System offer force-multiplying pliers to apply and measure cable tension. To facilitate cable tension measurement, the Howmedica system uses a beam deflection torque wrench connected to the drive mechanism of the pliers, and the DePuy system uses a tension gauge built into the tensioning pliers. Each of these systems, however, only measures tension before the cable is secured. After securing the cable, for example by crimping a cable retainer, cable tension frequently decreases dramatically due to inadvertent oblique loading during the crimping process. In addition, after the implantation of the tensioning system, post-operative shifting of bone fragments and slippage of the cable in the securing mechanism may also contribute to loss of cable tension.

SUMMARY OF THE INVENTION

A tensioning system according to various aspects of the present invention provides dynamic tensioning to maintain high tension in a fixation system despite tissue shifting, cable slippage, or other inadvertent loss of tension. In particular, an exemplary embodiment of an in-line dynamic tensioning system includes a dynamically tensioning cable retainer, suitably comprising a suture anchor or bone screw, which provides a bias to maintain tension in the cable after installation. The retainer includes a retaining mechanism for retaining the cable or suture and a biasing mechanism connected to the retaining mechanism. In the event of cable slippage or slackening, the biasing mechanism tends to take up the slack and maintain tension. As a result, cable tension is maintained regardless of inadvertent cable slackening after installation.

BRIEF DESCRIPTION OF THE DRAWING

The subject matter of the present invention is particularly pointed out and distinctly claimed in the concluding portion of the specification. The invention, however, both as to organization and method of operation, may best be understood by reference to the following description taken in conjunction with the claims and the accompanying drawing, in which like designations denote like elements and:

FIG. 4 illustrates a further alternative exemplary medical tensioning system using an in-line biasing mechanism;

FIGS. 6A–C illustrate a further alternative exemplary medical tensioning system using an in-line biasing mechanism comprising a loop and a Belleville spring;

FIGS. 11A–B illustrate an alternative in-line tensioning system comprising a suture anchor including a sleeve;

FIGS. 12A–B illustrate another alternative in-line tensioning system comprising a suture anchor including a sleeve;

FIGS. 13A–B illustrate an alternative in-line tensioning system comprising a suture anchor including an alternative spring;

DETAILED DESCRIPTION OF PREFERRED EXEMPLARY EMBODIMENTS

Figure 1:
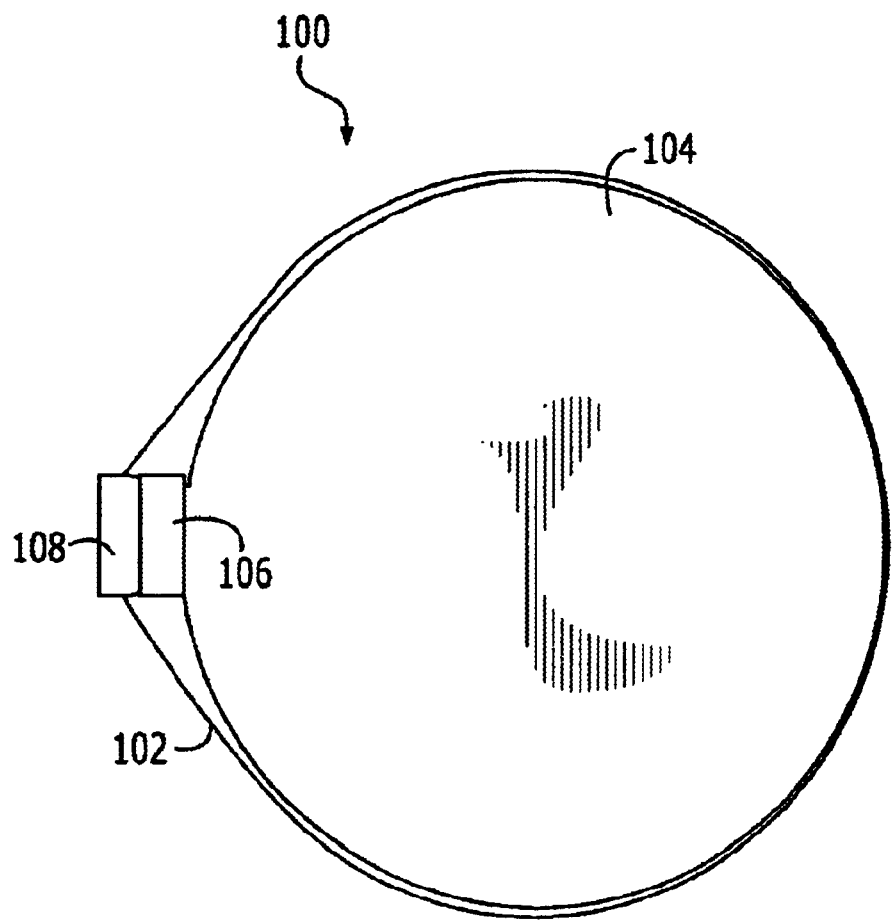
FIG. 1 illustrates a medical tensioning system according to various aspects of the present invention.

Referring now to FIG. 1, a medical tensioning system 100 according to various aspects of the present invention comprises a cable 102 for disposition around a structure, such as a bone 104; a retainer 108 for retaining cable 102; and a biasing mechanism 106 suitably configured for maintaining cable tension, after installation, such as due to slackening of the cable 102. The medical tensioning system 100 is suitably implantable, such as into human or animal tissue. The medical tensioning system 100 may be used in conjunction with nearly any anatomical structure, for example and solely by way of illustration, an approximately cylindrical bone such as a femur, humerus, radius, tibia, hip stem, or sternum. In addition, the medical tensioning system 100 may be suitably adapted to any anatomical location or application, such as trochanteric reattachment or fixation of high tibial osteotomies. The bone 104 is depicted as circular in FIG. 1 for convenience of reference; however, it should be appreciated that the bone 104 may be of any shape suitable for binding with the cable 102 of the present embodiment.

The cable 102 is looped circumferentially around the exterior of the bone 104 to maintain the bone's 104 shape, position, and/or integrity. Accordingly, the cable 102 may comprise any medical tensioning cable or wire now known or to be devised in the future, conventional or otherwise, of suitable strength and flexibility. For example, the cable 102 suitably comprises a single wire. Alternatively, the cable 102 may comprise a multistrand cable for added flexibility and strength. Further, the cable 102 may comprise a relatively broad, flat band, such as a Parham band, or may comprise a suture. In accordance with a preferred aspect of the present invention, the cable 102 comprises any suitable biocompatible material for implantation into biological tissue. For example, a suitable cable 102 comprises a multistrand cable comprising a bundle of individual fibers of biocompatible material, preferably of high tensile strength and flexibility, such as titanium alloy, cobalt chromium alloy, or stainless steel.

To retain the bone's 104 shape and position, the cable 102 is placed under tension. For example, after the cable 102 is disposed around the bone 104, the cable 102 is tensioned using any suitable tensioning mechanism. Suitable tensioning tools include force multiplying pliers or screw thread-activated spreading tools.

After the cable 102 is disposed around the bone 104 and placed under tension, in accordance with a potentially preferred aspect of the present invention, the cable 102 is retained in a retainer 108. The retainer 108 is suitably configured to secure the ends of the cable 102 in relatively constant relation to each other. As so configured, the retainer 108 preferably tends to prevent slippage of the cable 102 which tends to reduce the tension in the cable 102 and consequently induce slack. For example, referring now to FIGS. 2A–C, and in accordance with one aspect of the present invention, a suitable retainer 108 includes a crimp block 110 having two holes 112, suitably parallel, formed therethrough. The holes 112 formed in the crimp block 110 are sufficiently large to receive the ends of the cable 102 relatively freely. The ends of each hole 112 are suitably beveled to facilitate insertion of the cable 102 into each hole 112. After the cable 102 is suitably disposed around the bone 104 and placed under tension, the ends of the cable 102, disposed through the holes 112 in crimp block 110, are secured, for example by crimping the sides of the crimp block 110. Such crimping, while tension is maintained on the cable 102, may be accomplished, for example, through the use of pliers. The normal action of the pliers serves to reduce the size of the holes 112, thereby clamping the ends of the cable 102 in position within the crimp block 110. While the retainer 108 thus described preferably comprises a crimp type retainer, it should be appreciated that the retainer 108 may comprise any suitable mechanism for retaining the ends of the cable 102 in position and substantially maintaining tension in the cable 102 during retention.

In accordance with various aspects of the present invention, the biasing mechanism 106 is suitably configured to dynamically maintain tension in the cable 102 despite inadvertent loss of cable tension as may be caused by, for example, shifting of bone fragments or slipping of the cable 102 in the retainer 108. The biasing mechanism 106 suitably operates in conjunction with the bone 104 and is suitably responsive to tension in the cable 102. For example, in accordance with a preferred aspect of the present invention, the biasing mechanism 106 responds to a reduction in the tension in the cable 102 and adds tension to compensate for slackening. The biasing mechanism 106 suitably includes a spring, a resilient material, or an analogous mechanism disposed between the retainer 108 and the bone 104, or alternatively, disposed in line with the cable 102.

Figure 2C:
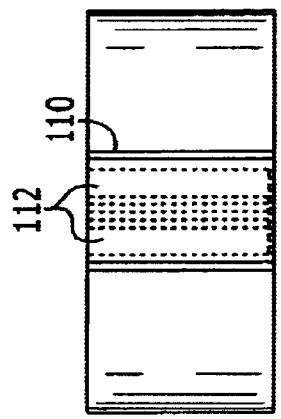
FIGS. 2A–C illustrate perspective, elevational, and top views, respectively, of an exemplary dynamically tensioning cable retainer for the medical tensioning system of FIG. 1.
Figure 2A:
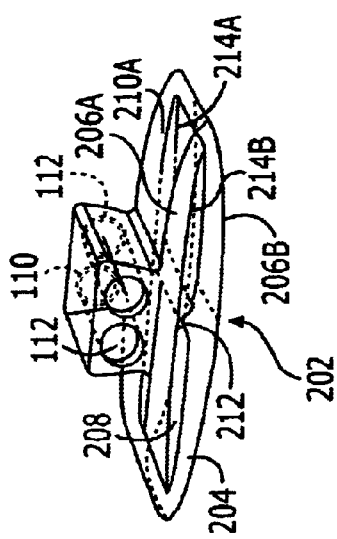
Figure 2B:
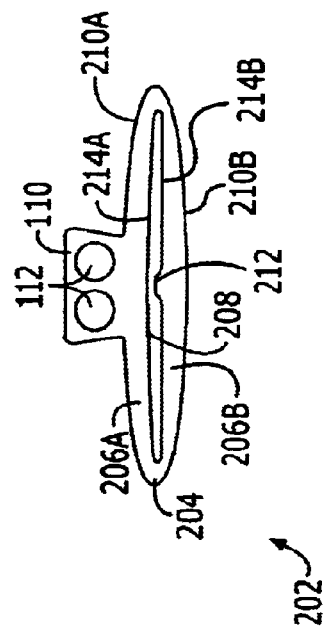

Referring to FIGS. 2A–C, in accordance with a first embodiment of the present invention, the medical tensioning system 100 includes a spring 204 formed integrally with the crimp block 110 to form a dynamically tensioning retainer 202. The retainer 202 is suitably formed of a durable, biocompatible material, such as cobalt chromium alloy, titanium alloy, stainless steel or the like. The retainer 202 suitably comprises the crimp block 110 described above having first and second holes 112 formed therethrough and a biasing mechanism 106, such as the spring 204, formed integrally with the crimp block 110. The spring 204 suitably comprises a leaf spring having, for example, two relatively stiff but resilient leaves 206A–B. The leaves 206A–B are suitably positioned substantially parallel to each other and joined at each end. Further, the leaves 206A–B are preferably biased to curve in opposite directions, forming a space 208 between the leaves 206A–B. In such a configuration of the spring 204, when force is applied to the outer surfaces 210A–B of the leaves 206A–B, the leaves 206A–B deform and partially collapse the space 208 formed between the leaves 206A–B. Conversely, as the force on the outer surfaces 210A–B of the leaves 206A–B is relieved, the leaves 206A–B separate and return to their original configuration.

To maintain a desired minimum separation between the leaves 206A–B, a spacer 212 is suitably disposed between the leaves 206A–B. The spacer 212 may comprise any rigid or resilient material for maintaining separation between the inner surfaces 214A–B of the leaves 206A–B. For example, the spacer 212 suitably comprises a semi-cylindrical protrusion formed in the inner surface 214B of the lower leaf 206B. With such a configuration, as force is applied to the outer surfaces 210A–B of the leaves 206A–B and the space 208 between the leaves 206A–B collapses, the inner surface 214A of the upper leaf 206A abuts the spacer 212, which in turn tends to prevent further collapse of the leaf spring 204.

In accordance with this illustrated embodiment, the spacer 212 may also serve as an indicator of appropriate tension. For example, the materials and configuration of the leaf spring 204 may be selected to require a particular force, such as 100 pounds, on the outer surfaces 210A–B of the leaf spring 204 to collapse the leaf spring 204 such that the upper leaf 206A contacts the spacer 212. Thus, when the cable 102 is sufficiently tensioned to force the upper leaf 206A into contact with the spacer 212, the system communicates to the user (e.g., the surgeon) that the cable tension is placing 100 pounds of force onto the leaf spring 204. With this parameter established the tension on the cable 102 may then be determined accordingly.

Referring again to FIGS. 1 and 2A-C, the retainer 202 preferably dynamically maintains tension in the cable 102 disposed around the bone 104. Initially, the cable 102 is wrapped around the bone 104 and the retainer 202 is positioned on the surface of the bone 104. The retainer 202 is suitably positioned such that the outer surface 210B of the lower leaf 206B abuts the bone 104, and the holes 112 in the crimp block 110 are parallel to the plane of the cable 102.

The ends of the cable 102, being suitably disposed through and retained in the holes 112 in the crimp block 110, are thus placed under suitable tension. As the tension is applied to the cable 102, a corresponding force is applied to the upper leaf 206A such that the upper leaf 206A collapses toward the lower leaf 206B abutting the bone 104. Once the appropriate tension is applied to the cable 102, the leaf spring 204 suitably substantially completely collapses so that the upper leaf 206A abuts the spacer 212. The crimp block 110 is then crimped to hold the cable 102 in position and substantially maintain tension on the cable 102.

Figure 3:
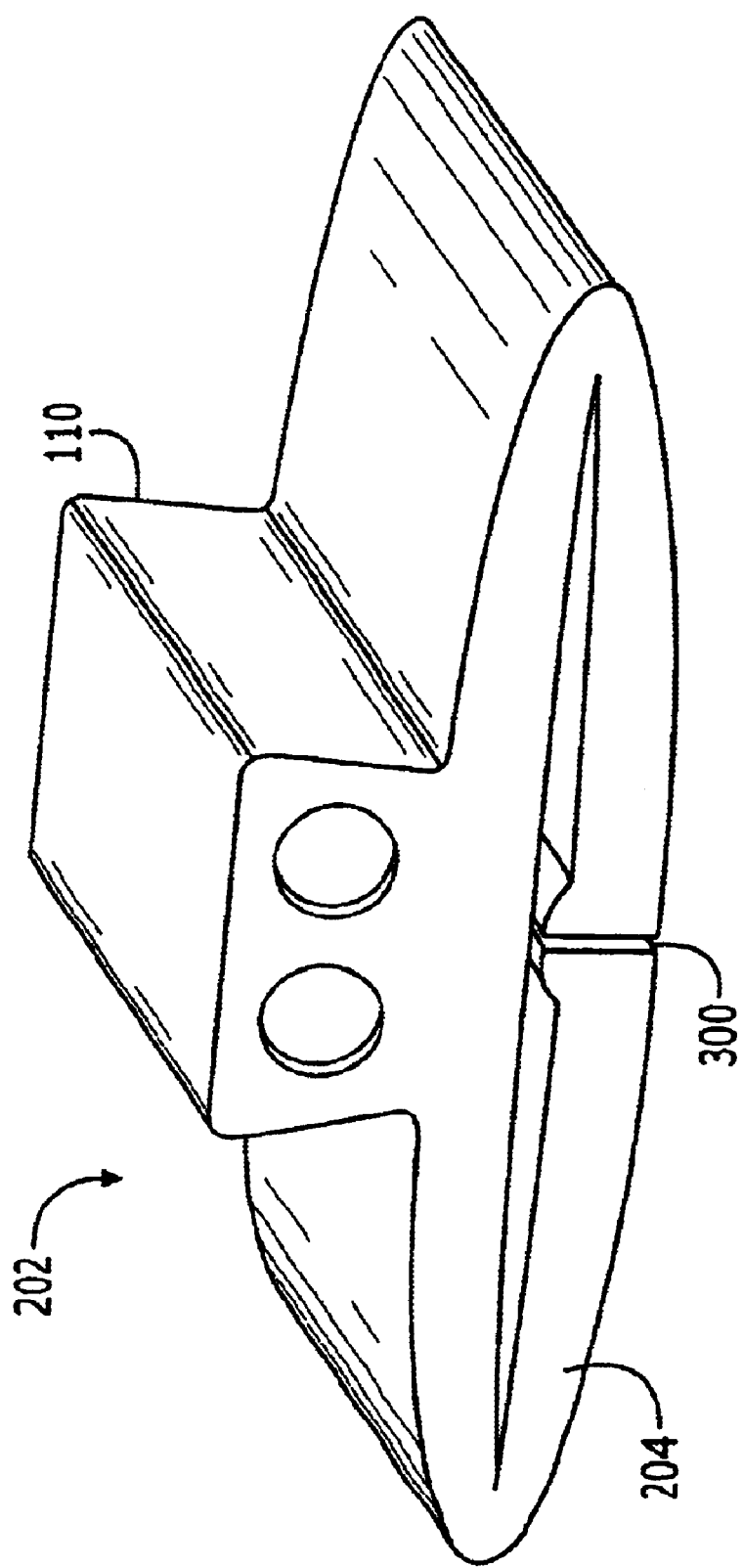
FIG. 3 illustrates one alternative embodiment of the cable retainer of FIGS. 2A–C having a slotted lower leaf.

In the event that the cable 102 loses tension, for example due to shifting of bone fragments, the retainer 202 maintains tension in the cable 102. For example, and in accordance with a preferred aspect of this illustrated embodiment, as the cable 102 slackens due to loss of tension, the spring 204 pushes the crimp block 110 away from the bone 104, suitably with an approximate force according to a typical spring equation:

$$f = kx$$

where f is force exerted by the spring 204, x is the displacement of the crimp block 110 from its relaxed state, and k is the spring constant for the spring 204. The spring constant corresponds to the stiffness of the spring 204. The spring constant may be varied to achieve different compression forces for different applications, for example by altering the materials and configuration of the spring 204. For example, to achieve relatively low compression forces, the lower leaf 206B may include a slot 300, as shown in FIG. 3, to facilitate collapse of the space 208 with relatively low forces. In the present embodiment, the outward force exerted by the spring 204 tends to maintain tension, even as slack develops in the cable 102.

Figure 8:
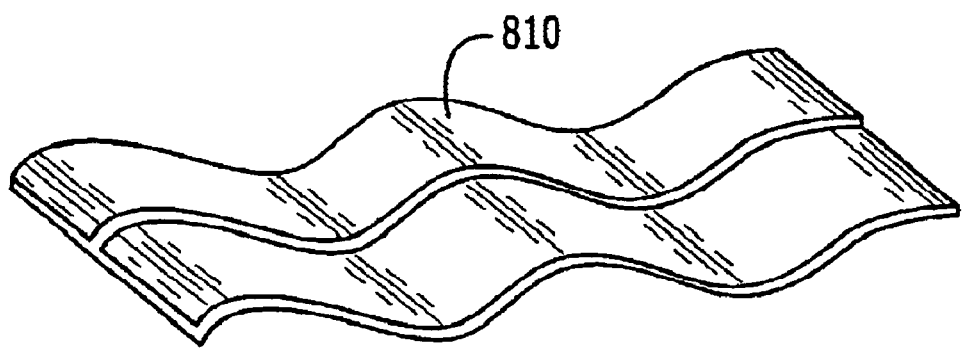
FIG. 8 illustrates an exemplary ribbon spring.

Other suitable biasing mechanisms 106 may be alternatively used instead of the spring 204, as may be now known or hereafter devised by those skilled in the art. For example, a helical compression spring or a resilient material may be disposed between the bone 104 and the cable 102 or the crimp block 110 to force the cable 102 away from the bone 104 and suitably maintain tension in the cable 102. In addition, a ribbon spring, such as the ribbon spring 810 of FIG. 8, may be similarly disposed between the bone 104 and the cable 102 or the crimp block 110 to suitably maintain tension in the cable 102.

Figure 3A:
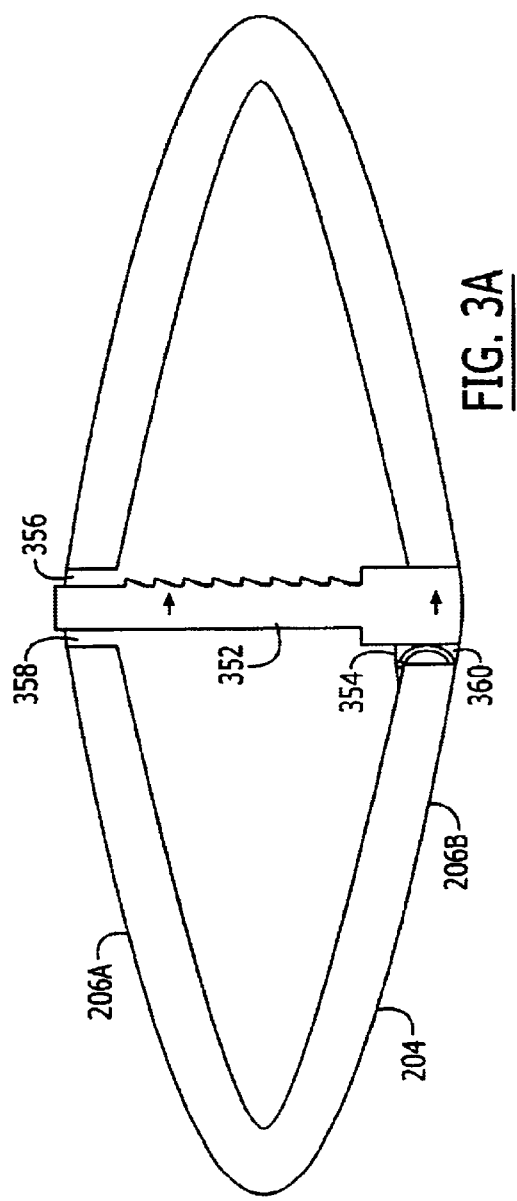
FIGS. 3A–B illustrate an alternative embodiment of the biasing mechanism having a unidirectional deployment mechanism.
Figure 3B:
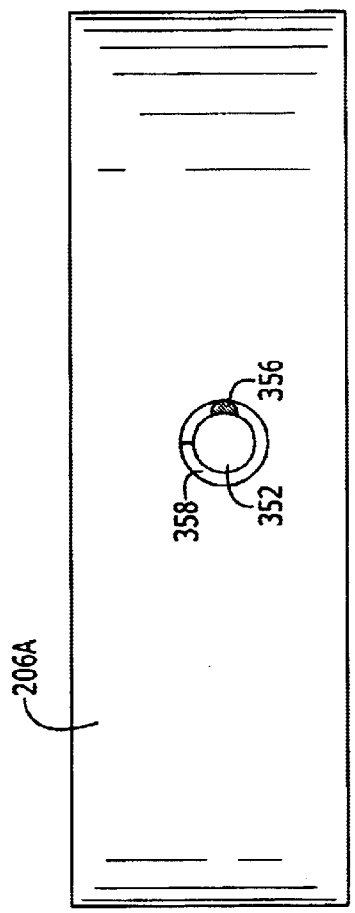

The biasing mechanism 106 may also include a mechanism for establishing unidirectional deployment. For example, the biasing mechanism 106 suitably includes a ratcheting system so that any loss of compression of the leaf spring 810 is retained even when tension in the cable 102 is increased. For example, referring to FIGS. 3A–B, a ratcheting system 350 suitably comprises a notched post 352, a post biasing mechanism 354, and a post interface 356. The notched post 352 is suitably attached to the lower leaf 206B and extends toward the upper leaf 206A of the leaf spring 204. The upper leaf 206A suitably includes a hole 358 through which the upper end of the notched post 352 is received, thus facilitating the movement of the upper leaf 206A with respect to the lower leaf 206B. It should be noted that unidirectional deployment may be featured in any number of suitable biasing mechanisms other than leaf springs. Further, suitable alternative mechanisms for implementing unidirectional deployment may be used, such as an obstruction unidirectionally biased towards the seam joining the two leaves of the leaf spring. As the leaves spread, the obstruction approaches the seam and is prevented from retracting. As a result, the leaves are retained in the spread position and cannot be substantially compressed.

The notched post 352 includes multiple notches or ridges formed on an external surface of the notched post 352. The notches are configured to engage the post interface 356, which is suitably formed on the interior surface of the hole 356 in the upper leaf 206A. The post interface 356 is preferably adapted to facilitate motion of the notched post 352 with respect to the upper leaf 206A in a selected direction and inhibit such motion in the other. In the present embodiment, the notches comprise teeth having an upper surface extending substantially perpendicularly away from the external surface of the post 352 and a lower surface disposed at an angle to the post's external surface. The post interface 356 suitably comprises the interior surface of the hole 358 and the bottom surface of the upper leaf 206A. The bottom surface of the upper leaf 206A suitably engages the upper surface of one of the teeth to inhibit inadvertent compression of the leaf spring 204. On the other hand, when the leaf spring 204 decompresses, the interior surface of the hole 358 slides over the angled lower surface of the tooth to facilitate expansion.

In the present embodiment, the notched post 352 is resiliently mounted on the lower leaf 206B so that the upper end of the notched post 352 may move laterally within the hole 358. The lateral motion facilitates moving the post 352 to accommodate initial compression of the spring and eventual expansion of the spring. In the present embodiment, the post biasing mechanism 354 biases the post 352 to engage the post interface 356. The post biasing mechanism 354 may comprise any suitable mechanism for biasing the post 352, such as a spring 360 mounted at the base of the post 352.

In accordance with a further embodiment of the present invention, a suitable biasing mechanism 106 may be positioned in series with the cable 102 to maintain tension. For example, referring now to FIG. 4, an alternative retainer 400 is suitably configured to dynamically tension and retain the ends of the cable 102, for example with a pair of crimps 402, and includes a biasing mechanism 106 associated with the crimps 402. The biasing mechanism 106 suitably comprises a high tension spring, such as a helical spring, leaf spring, Belleville spring, elastic material or the like. After the cable 102 is disposed around the bone 104 and tensioned, the ends of the cable 102 are crimped within the crimps 402. As slack develops in the cable 102, the biasing mechanism 106 contracts to pull the cable 102 taut. The tension placed on the cable 102 as the biasing mechanism 106 contracts is suitably proportional, as described above, to the characteristics of the biasing mechanism 106, such as the spring constant, and the displacement of the ends of the cable 102 relative to each other.

In another embodiment, the biasing mechanism 106 is incorporated into an anchor component, such as a suture anchor or a bone screw. Referring now to FIGS. 9–15, a dynamically tensioning anchor component 900 suitably comprises a securing component 902, an attachment component 904, and the biasing mechanism 106. The securing component 902 suitably comprises a structure which securely engages a selected structure, such as a bone. The attachment component 904 comprises a structure to which the cable or suture is attached. To provide dynamic tensioning, the biasing mechanism 106 is connected to the securing component 902 and the attachment component 904 to take up any slack that may develop in the cable or suture 102.

Figure 9A:
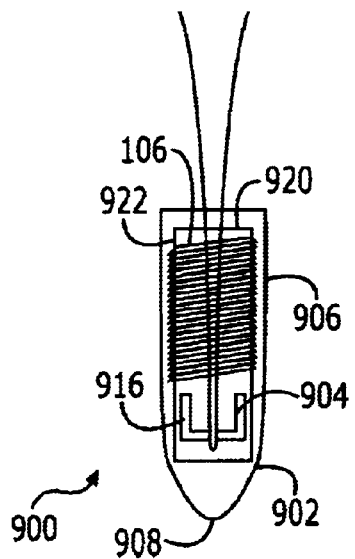
FIGS. 9A–C illustrate an alternative in-line tensioning system comprising a suture anchor.
Figure 9B:
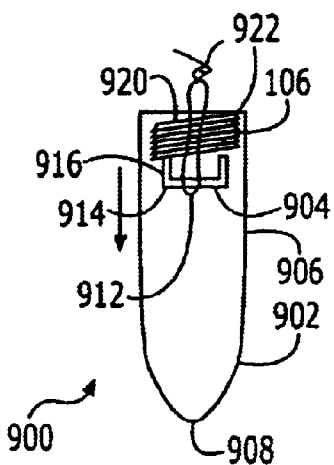
Figure 9C:
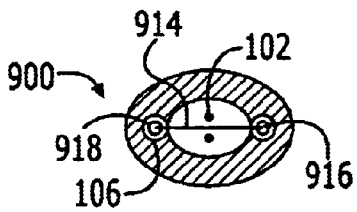
Figure 10A:
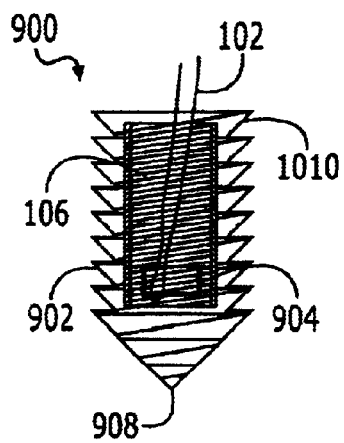
FIGS. 10A–B illustrate another alternative in-line tensioning system comprising a threaded suture anchor.
Figure 10B:
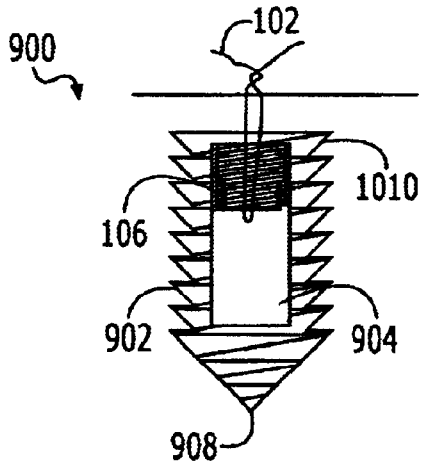
Figure 14A:
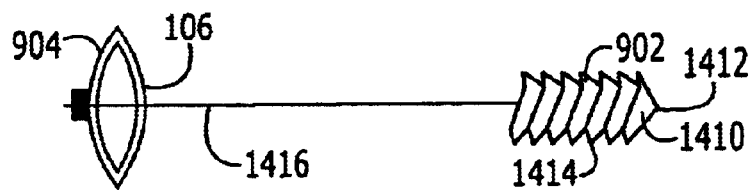
FIGS. 14A–C illustrate an embodiment of an in-line tensioning system comprising a bone screw.
Figure 14B:
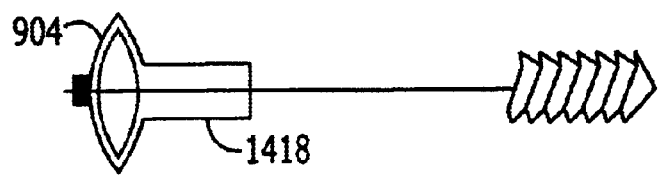
Figure 14C:
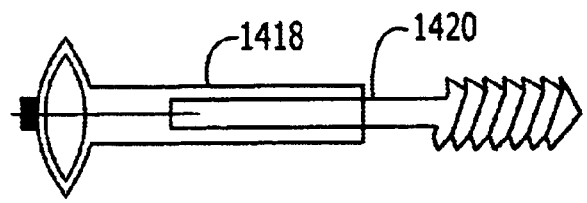
Figure 14D:
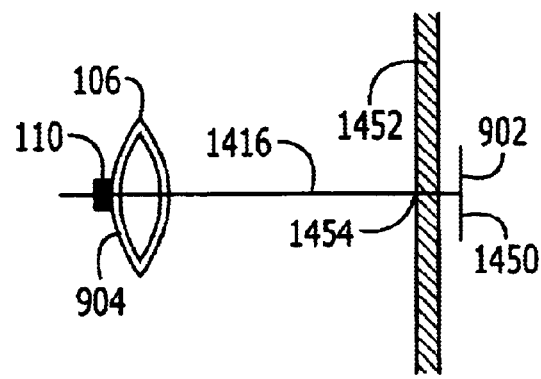
FIG. 14D illustrates an embodiment of an in-line tensioning system comprising a T-shaped anchor.

For example, referring to FIGS. 9–11, the securing component 902 comprises a suitable mechanism for attaching the anchor component 900 to a location. The securing component 902 may be configured for particular applications, such as to engage bone or other tissue. In one embodiment, the securing component 902 comprises a hollow cylinder 906 composed of biocompatible material. The cylinder 906 may include a point 908 at an end to facilitate embedding the securing component 902 in the tissue. Alternatively, the end to be embedded in the tissue may be open to form a sleeve 1110 (FIGS. 11A–B). Further, the securing component 902 may also have a threaded exterior surface 1010 (FIGS. 10A–B) to allow the anchor component 900 to be screwed into the tissue. Alternatively, the securing component's 902 outer surface may be substantially smooth, and held in position with cement, friction, or other suitable mechanism.

The attachment component 904 suitably secures the anchor component 900 to a medical tensioning system component, such as a cerclage wire or suture 102. The attachment component 904 may comprise any suitable mechanism for attaching the suture or wire 102 to the anchor component 900. In one embodiment, the attachment component 904 comprises a pin 912 slidably disposed within the hollow interior of the securing component 902. For example, the pin 912 suitably comprises a cross-member 914 oriented across the diameter of the hollow interior of the securing component 902. The cross-member 914 is connected to a pair of guide posts 916 slidably disposed within a pair of guide channels 918 formed in the interior surface of the securing component 902. The suture or wire 102 may be connected to or wrapped around the cross-member 914, and the pin 912 may slide along the axial length of the securing component 902 while maintaining its orientation across the securing component 902.

Alternatively, the attachment component 904 suitably comprises a piston 1112 slidably disposed within the hollow interior of the securing component 902. The piston 1112 suitably comprises a head 1114 for maintaining the orientation of the piston 1112 within the securing component 902 and an eyelet 1116 for connecting to the suture or wire 102. The head 1114 comprises any suitable configuration for maintaining movable contact with the interior surface of the securing component 902. For example, the head 1114 suitably comprises a cylinder or bullet-shaped structure composed of biocompatible material having an outer surface in slidable contact with the interior surface of the securing component 902. The eyelet 1116 is attached to the head 1114. The eyelet 1116 comprises any suitable structure for fastening the attachment component 904 to the suture or wire 102. For example, the eyelet 1116 suitably comprises a post 1118 having a first end attached to the head 1114 and a second end having a hole 1120 formed in it. The hole 1120 is suitably sized and configured to receive the suture, wire, or other material 102.

The biasing mechanism 106 interacts with the securing component 902 and the attachment component 904 to maintain the desired tension in the suture, wire, or other material 102. Generally, the biasing mechanism 106 is suitably configured to dynamically maintain tension in the cable 102 despite inadvertent loss of tension. The biasing mechanism 106 operates in conjunction with the securing component 902 and is suitably responsive to tension in the cable 102 via the attachment component 904. For example, in accordance with a preferred aspect of the present invention, the biasing mechanism 106 responds to a reduction in the tension in the cable 102 and adds tension to compensate for slackening. The biasing mechanism 106 suitably includes a spring, a resilient material, or an analogous mechanism disposed between the securing component 902 and the attachment component 904.

In one embodiment, for example, the biasing mechanism 106 comprises a compressed helical spring 920 having a first end engaging an annular lip 922 formed around the open end of the securing component 902 and a second end engaging the posts 916 of the pin 914 or the head 1114 of the attachment component 904. Consequently, as slack develops in the suture, wire, or other material 12, the spring 920 forces the attachment component 904 deeper into the securing component 902, thus removing slack. In another embodiment, the biasing mechanism 106 comprises a leaf spring 1310 inserted into the hollow interior of the securing component 902 (FIGS. 13A–B). The suture or wire 102 is suitably attached to the leaf spring 1310, for example at a point on the lower portion of the leaf spring 1310 such that the suture or wire 102 at the attachment point is biased downward and deeper into the securing component 902. In yet another embodiment, the biasing mechanism 106 comprises an expandable substance 1210 retained within the hollow interior of the securing component 902 (FIGS. 12A–B). The expandable substance 1210 may comprise any material which tends to expand or swell under selected conditions. For example, the expandable substance 1210 may comprise a hydrophilic substance which, upon absorbing fluid, tends to expand, thus biasing the attaching component 904 deeper into the securing component 902. Alternative materials may also be used, including materials that expand with application of heat (such as body heat) and the like.

In alternative embodiments, the securing component 902 may be separated from the attachment component 904. For example, referring now to FIGS. 14A–D, the securing component 902 suitably comprises a rigid structure 1410 having a point 1412 for driving into a surface, such as a bone, and a threaded exterior 1414 for screwing into the surface. Alternatively, the securing component 902 may comprise a post 1450 (FIG. 14D) which may be inserted through a small hole 1454 formed through a structure, such as a bone structure 1452, and deployed across the diameter of the hole 1454 to brace against the opposing surface. In addition, the securing component 902 suitably includes a mechanism for attaching a connector 1416, such as a wire or suture. The connector 1416 is suitably connected to the attachment component 904. Further, the attachment component 904 is suitably integrated into the biasing mechanism 106. For example, the attachment component 904 suitably comprises the crimp block 110 and the biasing mechanism 106 suitably comprises a spring 204, as described above in conjunction with the dynamically tensioning retainer 202. The dynamically tensioning retainer 202 suitably further includes an integrated sleeve 1418 to maintain the position of the connector 1416 with respect to the dynamically tensioning retainer 202 and the securing component 902. In another embodiment, rigidity may be provided by adding a shaft 1420 to the securing component 902. The shaft 1420 suitably extends into the hollow integrated sleeve 1418 to inhibit lateral movement in any direction other than the direction in which tension is applied.

To install the dynamically tensioning anchor component 900, the securing component 902 is suitably fixed at a desired location. The connector 1418 is then suitably placed under the appropriate tension. The dynamically tensioning retainer 202 is then suitably braced against a desired structure and compressed, and the connector 1418 may then be threaded through the holes of the crimp block 110. The crimp block 110 is then crimped with the connector 1418 under tension to retain the connector 1418.

In yet another embodiment, the dynamically tensioning retainer 202 may be replaced with a different biasing mechanism 106. In addition, the attachment component 904 suitably abuts a tissue or structure instead of connecting to a wire, suture, or other material. For example, referring now to FIGS. 15A–C, a dynamically tensioning anchor component 900 is suitably configured as a dynamically tensioning bone screw. One embodiment includes a securing component 902 having a point 1510 and a threaded exterior surface 1512 to facilitate being driven into a bone or other structure. In addition, the securing component 902 includes a shaft 1514 which is terminated by a cap 1516. The attachment component 904 suitably comprises a sleeve 1518 and a head 1520. The sleeve 1518 is suitably hollow and configured to receive the cap 1516 and the shaft 1514. The sleeve 1518 further suitably includes an inwardly extending flange 1522 at its end. Further, the sleeve 1518 may include a threaded exterior surface 1524. The biasing mechanism 106 is suitably inserted between the securing component 902 and the attachment component 904, for example to bias the securing component 902 and the attachment component 904 towards each other. For example, a compressed helical spring 1526 may be disposed between the cap 1516 of the shaft 1514 and the flange 1522 of the sleeve 1518, around the shaft 1514, and within the hollow sleeve 1518.

To facilitate driving the screw, the attachment component 904 suitably includes a tool interface, such as a hexagonal cavity 1530 to receive a hexagonal wrench, formed in the head 1520. To transfer torque to the securing component 902, a suitable torque interface may be provided. For example, the torque interface suitably includes a hexagonal outer surface 1532 formed on the exterior of the shaft 1514 or the outer rim of the cap, and a hexagonal interior surface 1534 formed on the interior of the flange 1522. Thus, the securing component 902 may move axially with respect to the attachment component 904, but torque applied to the attachment component 904 is transferred to the securing component 902 as well.

In another embodiment (FIG. 15B), the head 1520 includes a relatively large hexagonal cavity 1540 to receive a hexagonal wrench and a hole 1542 extending into the hollow interior of the sleeve 1518. An alternative torque interface further includes a relatively small hexagonal cavity 1544 formed in the cap 1516 of the securing component 902. Thus, the securing component 902 and the attachment component 904 may be driven into the desired structure relatively independently.

Figure 15A:
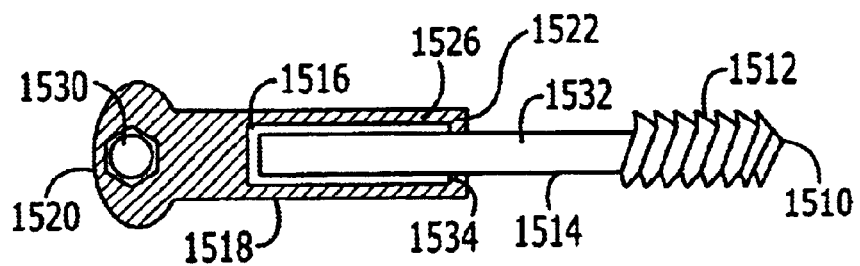
FIGS. 15A–C illustrate an alternative embodiment of an in-line tensioning system comprising a bone screw.
Figure 15B:
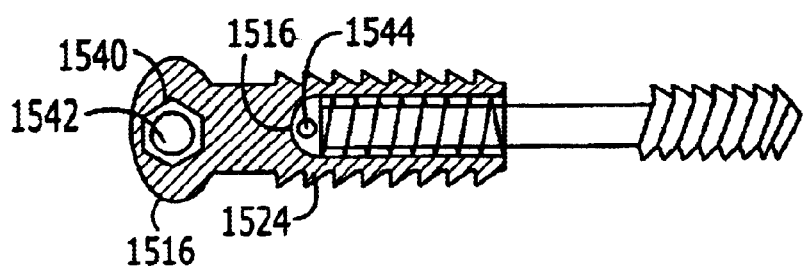
Figure 15C:
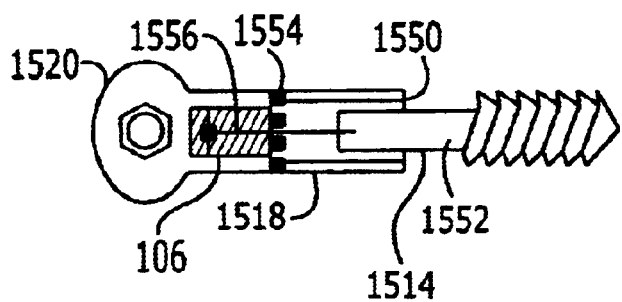

In yet another embodiment, the interior of the sleeve 1518 of the attachment component 904 is stepped (FIG. 15C). The distal end of the sleeve 1518 with respect to the head 1520 of the attachment component 904 is wider than the proximal end and has a hexagonal interior surface 1550. The hexagonal interior surface 1550 is suitably configured to engage a hexagonal exterior surface 1552 of the shaft 1514 of the securing component 902. Thus, torque applied to the attachment component 904 via the head 1520 is transferred to the securing component 902.

The proximal end of the sleeve 1518 is narrower than the distal end and suitably includes an inwardly extending flange 1554 near the boundary with the wider proximal cavity. The biasing mechanism 106, such as a compressed helical spring, is disposed between the flange 1554 and the end of the sleeve 1518. The end of the biasing mechanism 106 opposite the flange 1554 is suitably connected to the securing component 902, such as via a connector 1556 attached to the securing component 902. As the anchor component 900 is screwed into the structure, the head 1520 of the attachment component 904 may meet an obstruction, such as the outer surface of the bone. As torque continues to be applied to the anchor component 900, however, the securing component 902 suitably extends away from the attaching component as the force exerted by the biasing mechanism 106 increases. Thus, the biasing mechanism 106 tends to draw the attachment component 904 (and the structure it abuts) toward the securing component 902 (and the structure it engages).

Figures 5A, 5B:
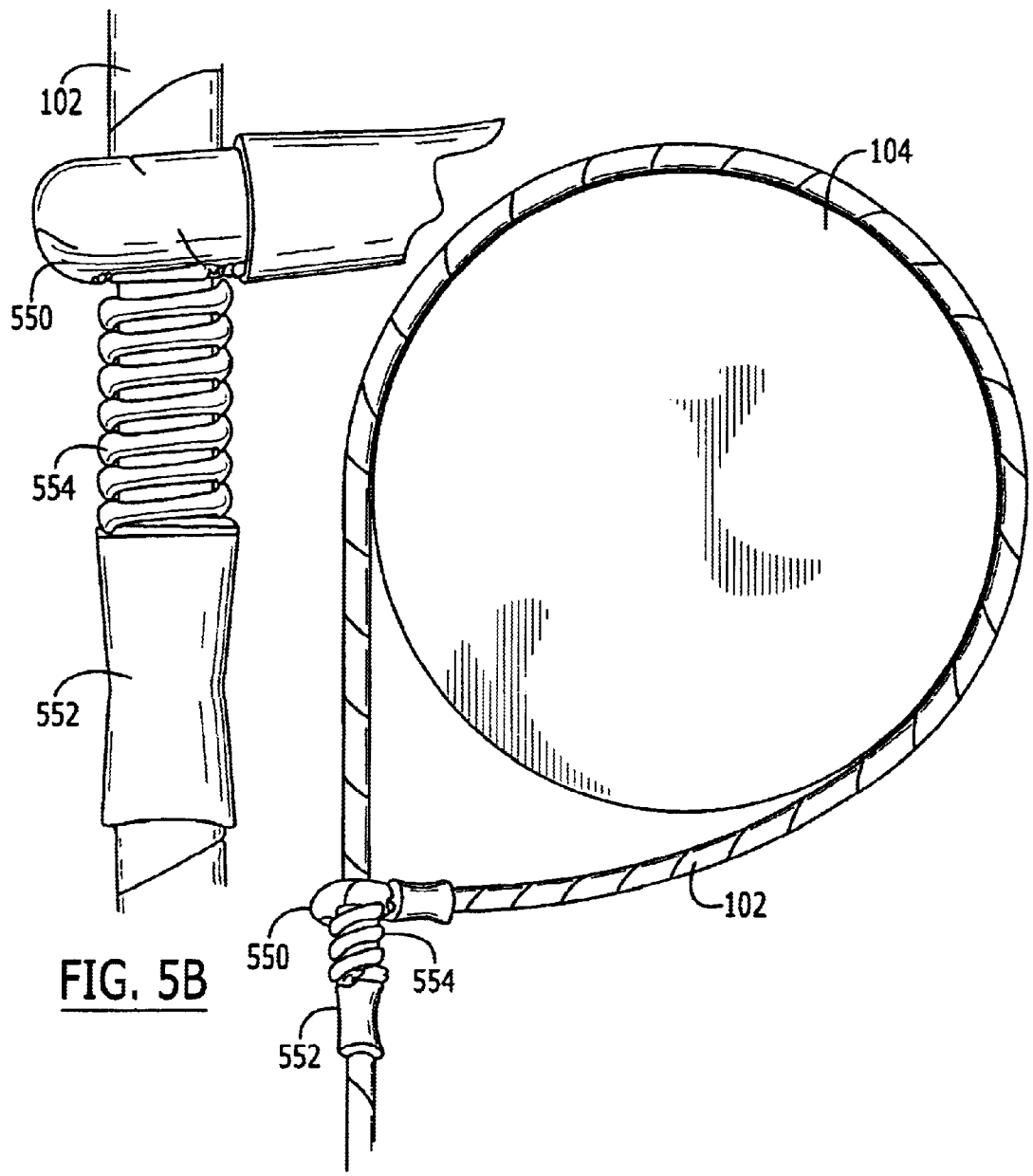
FIGS. 5A–B illustrate a further alternative exemplary medical tensioning system using an in-line biasing mechanism comprising a loop and a helical spring.

Alternatively, the retainer 400 and the biasing mechanism 106 may be configured separately. Referring now to FIGS. 5A–B, the retainer 400 suitably comprises a loop 550 formed in one end of the cable 102. The other end of the cable 102 is wrapped around the bone 104 and passed through the loop 550. The retainer 400 further suitably includes a block, for example a sleeve 552, fixed to the cable 102, suitably by crimping or other appropriate mechanism, to prevent the loop 550 from moving beyond the block. For example, the sleeve 552 has a sufficient diameter to prevent the loop 550 from passing over and around the sleeve 552. The biasing mechanism 106 is suitably disposed to maintain tension in the cable 102, for example between the loop 550 and the sleeve 552. The biasing mechanism 106 comprises any suitable biasing mechanism, for example a helical spring 554. Alternatively, the biasing mechanism 106 may comprise a Belleville spring 654 (FIGS. 6A–C). The biasing mechanism 106 suitably biases the loop 550 towards the bone 104 and away from the sleeve 552, thus tending to maintain tension in the cable 102.

Figure 7:
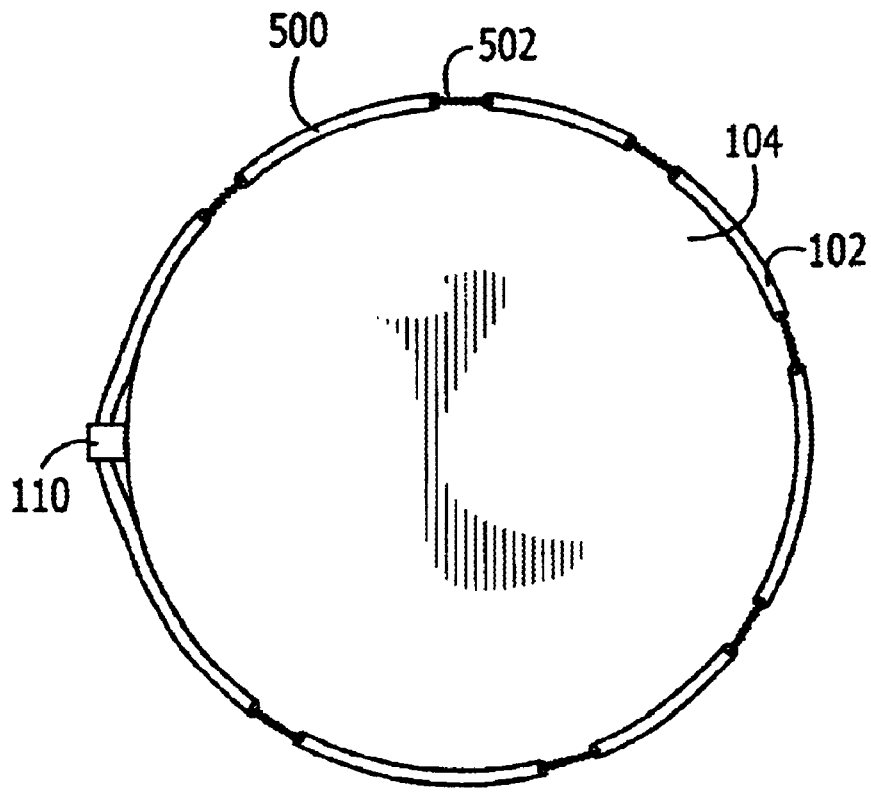
FIG. 7 illustrates a medical tensioning cable having a built-in biasing mechanism.

In yet another alternative embodiment of a system according to the present invention, the biasing mechanism 106 is suitably incorporated into the cable 102. Referring now to FIG. 7, in accordance with this embodiment, the cable 102 suitably comprises respective multiple segments 500 connected by respective elastic joints 502. The cable segments 500 suitably comprise any high tensile strength, biocompatible material, such as stainless steel cable, wire, or the like. The joints 502 comprise any suitable biasing mechanism, for example a resilient elastic material or a spring. Similarly, the cable 102 may be entirely comprised of a resilient, elastic material. In accordance with this embodiment, after the cable 102 is disposed around the bone 104 and suitably tensioned, the joints 502 or the cable 102 expand according to the magnitude of the tension on the cable 102. When the desired tension is achieved, the ends of the cable 102 are fixed in position, for example with a crimp block 110. As the cable 102 loses tension, for example due to shifting bone fragments, the joints 502 or the cable 102 tend to contract and maintain tension in the cable 102.

Figure 16:
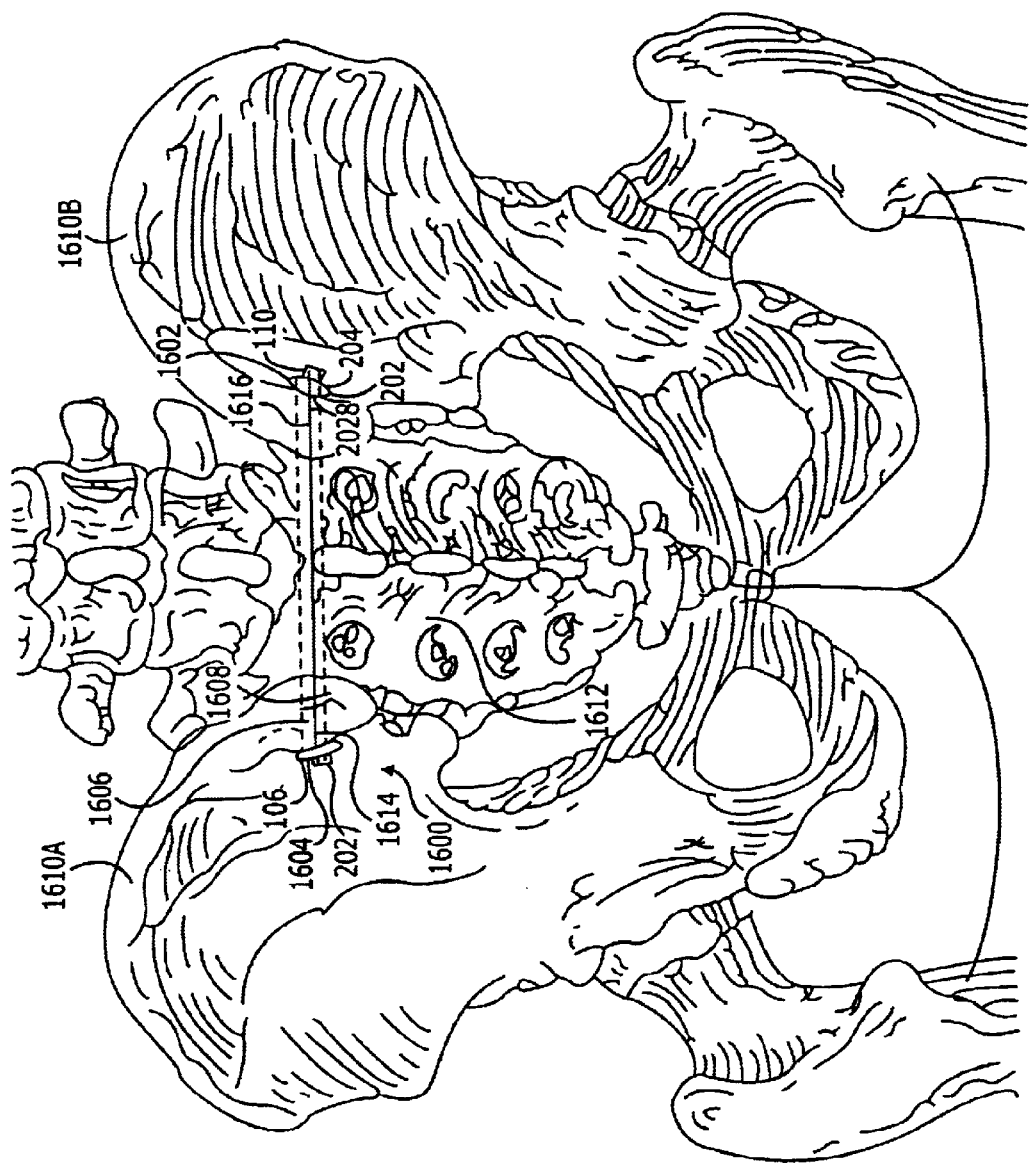
FIG. 16 illustrates an alternative embodiment of an in-line tensioning system for stabilizing a sacroiliac joint.

In another in-line configuration, a medical tensioning system according to various aspects of the present invention may be used to provide compression, such as to stabilize an anatomical structure. For example, a medical tensioning system may be configured to stabilize dislocated joint, such as by compressing sacroiliac joint dislocation. Referring now to FIG. 16, a suitable medical tensioning system 1600 comprises a biasing mechanism 1602, an anchor 1604, and a cable 1606. The cable 1606 is suitably disposed through a hole 1608 (denoted by broken lines in FIG. 16) formed through the anatomical structure to be supported. In particular, the hole 1608 may be formed, by conventional techniques, through one of the iliac crests 1610A, the sacral body 1612, and the other iliac crest 1610B to form a continuous, suitably linear, aperture. The hole 1608 is suitably of sufficient diameter to accommodate the cable 1606. The cable 1606 is threaded through the hole 1608.

A first end 1614 of the cable 1606 is suitably anchored to one of the iliac crests 1610A. For example, the first end 1614 of the cable 1606 may be anchored to the external surface of the first iliac crest 1610A, such as by tying the first end 1614 of the cable 1606 to or looping the cable 1606 around the anchor 1604, such as a post, disposed across the opening to the hole 1608. In one embodiment, the first end 1614 of the cable 1606 is retained by a dynamically tensioning retainer 202, for example as described below, such that the biasing mechanism 106 of the dynamically tensioning retainer 202 biases the first end 1614 of the cable 1606 away from the surface of the iliac crest 1610A and maintains tension in the cable 1606.

The second end 1616 of the cable 1606 is suitably connected to the biasing mechanism 1602. The biasing mechanism 1602 suitably comprises any mechanism for biasing the second end 1616 of the cable 1606 away from the external surface of the second iliac crest 1610B and maintaining tension in the cable 1606. In the present embodiment, the biasing mechanism 1602 suitably comprises a dynamically tensioning retainer 202 having a crimp block 110 and a leaf spring 204. The retainer 202 is situated over or near the opening of the hole 1608 such that at least a portion of the retainer's 202 bottom leaf 206B engages the outer surface of the second iliac crest 1610B. The crimp block 110 of the retainer 202 is suitably positioned on the opposite side of the spring 204 from the second iliac crest 1610B and retains the second end 1616 of the cable 1606.

The cable 1606 is threaded through the hole 1608 in the anatomic structure and connected to the anchor 1604. The cable 1606 is then placed under an appropriate amount of tension, and the second end 1616 of the cable 1606 is retained by the biasing mechanism 1602, for example within the crimp block 110. Thus, the cable 1606 extends through each iliac crest 1610A–B and the sacral body 1612. Each end of the cable 1606 is anchored to one of the iliac crests 1610A–B so that tension in the cable 1606 compresses the iliac crests 1610A–B towards the sacral body 1612. If slack develops in the cable 1606, the biasing mechanism 1602 takes up the slack in the cable 1606 and maintains tension in the cable 1606.

Figure 16A:
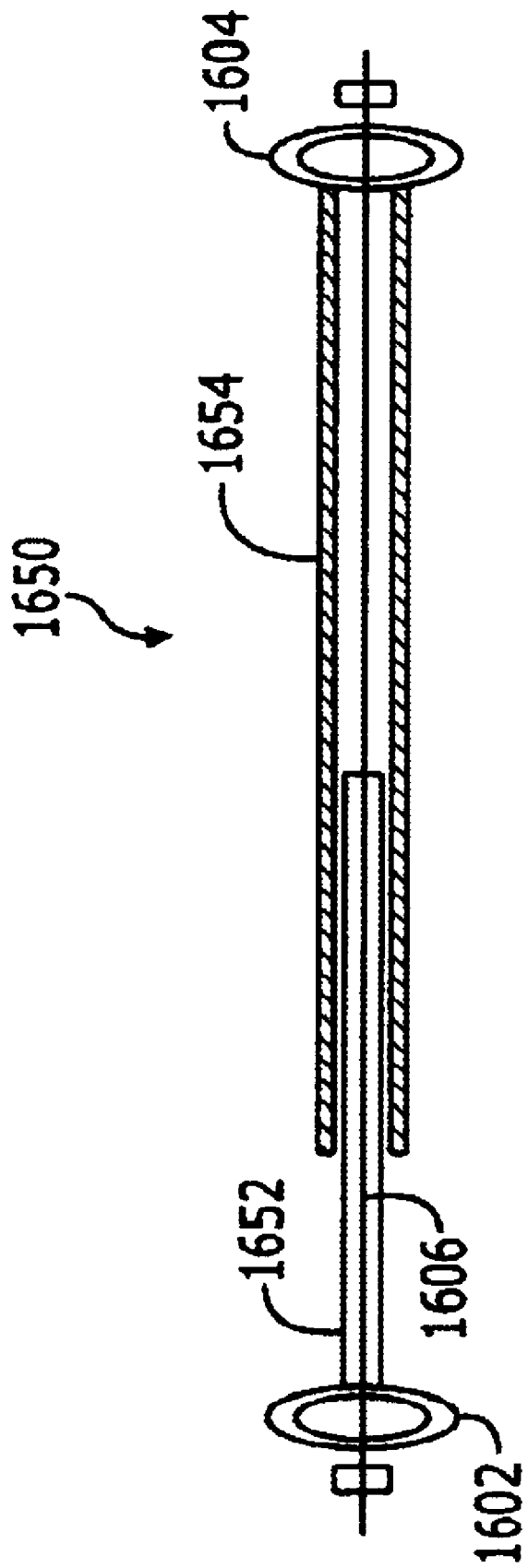
FIG. 16A illustrates an alternative embodiment of an in-line tensioning system for stabilizing a sacroiliac joint and inhibiting lateral bone movement.

In an alternative embodiment, the compression configuration may include a mechanism for lateral stabilization of the medical tensioning system. For example, a lateral stabilization mechanism may inhibit two bones or bone portions from shifting laterally. Referring now to FIG. 16A, a medical tensioning system 1650 according to various aspects of the present invention includes a lateral stabilization mechanism comprising a first hollow sleeve 1652 and a second hollow sleeve 1654. The first sleeve 1652 is rigidly connected to the biasing mechanism 1602, and the second sleeve 1654 is suitably rigidly connected to the anchor 1604. Alternatively, either or both of the sleeves 1652, 1654 may be connected to the biasing mechanism 1602 or the anchor 1604 in a nonrigid manner to facilitate optimal engagement of the bone surface. Each sleeve is threaded through the hole 1608 formed through the iliac crests and the sacral body. The hole 1608 is suitably of sufficient diameter to accommodate the sleeves 1652, 1654.

The first sleeve 1652 and the second sleeve 1654 are suitably configured in a telescoping manner so that the first sleeve 1652 slidably fits into the hollow interior of the second sleeve 1654 to facilitate movement of the sleeves with respect to each other along the longitudinal axis of the sleeves, but inhibit lateral movement of the sleeves 1652, 1654. The cable 1606 is disposed through the respective hollow interiors of the sleeves 1652, 1654 and suitably attached to the biasing mechanism 1602 and the anchor 1604.

In sum, a medical tensioning system according to various aspects of the present invention tends to dynamically tension and maintain cable tension in the presence of inadvertent or natural cable slippage or slackening. The biasing mechanism 106, disposed in line with the cable 102 or between the cable 102 and the bone 104, provides supplementary tension to take up slack due to cable slippage. Further, the biasing mechanism 106 may also serve to establish when a desired tension is achieved in the cable 102.

While preferred exemplary embodiments of the present invention have now been made clear, there will be immediately obvious to those skilled in the art many modifications of structure, arrangements, proportions, the elements, materials and components, used in the practice of the invention which are adapted for a specific environment and operating requirements without departing from the scope of the invention as expressed in the appended claims.

What is claimed is:

1. A device for dynamically maintaining tension on a flexible member affixed to an anatomical structure comprising:

means for attaching a flexible member thereto;

a securing component configured to be secured to an anatomical structure and comprising a generally cylindrical member having an opening at a top end;

means for retaining the securing component within a bone tunnel;

a biasing mechanism affixed to the securing component and connected to the attaching means, and configurable between a first position wherein the flexible member is under a first tension and a second position wherein the flexible member is under a second tension greater than the first tension, the biasing mechanism biased to increase tension in the flexible member, the biasing mechanism comprising a spring retainable within the cylindrical member and biased toward a bottom end of the cylindrical member; and wherein the flexible member attaching means comprises means for attaching the flexible member adjacent a bottom end of the spring.

2. The device recited in claim 1, wherein:

the securing component retaining means comprises a threaded outer surface of the cylindrical member for being screwingly inserted into the bone tunnel.

3. The device recited in claim 2, wherein the spring comprises a coil spring, and the attaching means comprises a pin disposed across the cylindrical member and means for retaining the pin beneath the spring, the flexible member in use following a path into the cylindrical member opening, downward through an interior of the spring, wrapping around the pin, and back upward out of the cylindrical member opening.

4. The device recited in claim 1, wherein the spring is substantially completely compressed in the first position, movement from the first position thereby unidirectional for taking up developed slack in the flexible member.

* * * * *